United States Patent [19]

Tsaprazis et al.

[11] Patent Number: 4,878,019

[45] Date of Patent: Oct. 31, 1989

[54] ELECTRICAL SENSING SYSTEM FOR MEASURING FERROUS PARTICLES WITHIN A FLUID WITH TEMPERATURE COMPENSATION CIRCUIT

[75] Inventors: Edward Tsaprazis, Havertown; Nicholas P. Maris, Lafayette Hills; Charles Montague, Media, all of Pa.

[73] Assignee: Aeroquip Corporation, Jackson, Mich.

[21] Appl. No.: 91,576

[22] Filed: Aug. 31, 1987

Related U.S. Application Data

[63] Continuation-in-part of Ser. No. 729,759, May 2, 1985, Pat. No. 4,731,578.

[51] Int. Cl.⁴ .................. G01N 27/74; G01R 33/12
[52] U.S. Cl. ................................. 324/204; 324/225; 324/232; 324/234; 340/631
[58] Field of Search ............. 324/204, 225, 232–234, 324/236, 237, 327, 59; 340/631; 331/65

[56] References Cited

U.S. PATENT DOCUMENTS

| | | | |
|---|---|---|---|
| 3,201,774 | 8/1965 | Uemura | 324/327 X |
| 3,340,466 | 9/1967 | Ono | 324/232 |
| 3,896,371 | 7/1975 | Hametta | 324/327 |
| 4,004,216 | 1/1977 | Natens et al. | 324/233 |
| 4,130,792 | 12/1978 | Sullivan | 324/327 |
| 4,219,805 | 8/1980 | Magee et al. | 324/204 X |
| 4,237,419 | 12/1980 | Tornblom et al. | 324/232 X |
| 4,263,553 | 4/1981 | Cook et al. | 324/327 |
| 4,355,281 | 10/1982 | Toth et al. | 324/232 |
| 4,473,799 | 9/1984 | Favre | 324/236 X |
| 4,503,392 | 3/1985 | Fastritsky et al. | 324/232 |
| 4,731,578 | 3/1988 | Tsaprazis | 324/204 |

Primary Examiner—Gerard R. Strecker
Attorney, Agent, or Firm—Lipton, Famiglio & Elman

[57] ABSTRACT

A magnetic sensor for the collection and measurement of ferrous particles through the use of an electronic tuned circuit is disclosed. The sensor contains an electrical inductance along with an integral magnet to attract ferrous particles suspended in the fluid. The ferrous particles collecting on the magnetic surface of the sensor causes a change in the inductance of the integral coil which is measured by an electronic circuit. The electronic circuit operating in conjunction with the sensor utilizes a parallel tuned resonant circuit and time variant frequency multiplying to eliminate undesired response changes of the tuned circuit due to the temperature change of the sensor. The sensor may be located in environmental conditions which include a large variation in ambient temperature. The disclosed invention provides for compensation of such undesired changes caused by temperature change so that the actual change of the inductance in the sensor can be monitored without interference. The signal output from the circuit disclosed is representative of the amount of ferrous debris accumulated on said sensor.

3 Claims, 9 Drawing Sheets

ELECTRICAL SENSING SYSTEM FOR MEASURING FERROUS PARTICLES WITHIN A FLUID WITH TEMPERATURE COMPENSATION CIRCUIT

REFERENCE TO PRIOR APPLICATION

This application is a continuation-in-part of patent application Ser. No. 06/729,759, filed 5/2/85, entitled "An Electrical Sensing System for Measuring Ferrous Particles Within a Fluid" by Edward Tsaprazis. The application resulted in the issuance of patent Ser. No. 4,731,578 issued on 3/15/88.

SUMMARY OF THE INVENTION

The disclosed invention relates to means for detecting and measuring ferrous particles in a fluid medium, and it is of particular use for detecting ferrous particles in the lubricant of an engine or mechanical transmission. In such an application, the monitoring of such particles may be utilized to give warning of malfunction or other mechanical breakdown of the engine or transmission. The invention disclosed if of particular importance for the operation of an internal combustion engine, especially highly stress helicopter and aircraft engines wherein prior warning of a malfunction permits corrective action prior to catastrophic failure.

Metal parts in the internal combustion or mechanical transmission, e.g., gear boxes, undergo wear because of friction between the metallic parts or a metal part and a non-metal part. The result of the wearing friction is metallic contamination of the lubricant or transmission fluid. The contamination comprises metal particles of many sizes and shapes. Monitoring of the metal particles contained in the fluid ca provide early warning of the deterioration of a mechanical device such as the internal combustion engine or its associated operating systems such as mechanical power transmissions or other gear boxes.

The present invention uses magnetic attraction to capture ferrous particles circulating in the fluid system. An electrical inductance coil situated around a permanent magnet is used as a probe for insertion into an oil gear box for the metering of metallic debris therein. As ferrous particles are captured on the permanent magnet containing the sensor probe, the electric inductance of the probe is thereby changed due to the proximity of the various particles through the coil. This change in inductance is used to change the operating frequency of an electrical bandpass filter. This change in operating frequency of the filter is monitored, and processed electronically to relate to the amount of debris accumulation upon the sensor probe.

A fixed frequency oscillator having two known, stable frequency outputs is used to drive the filter, alternatively in time, above and below its center resonant frequency. As the bandpass filter changes resonant frequency due to debris buildup, the associated electronic circuitry described herewith measures such a change in resonant frequency and presents the output in a form suitable for display.

An inherent problem in the monitoring for ferrous particles in a lubricant such as an aircraft power transmission is the problem of widely ranging temperature variation. The temperature of a transmission lubricant in an aircraft, or any other engine, can change many hundreds of degrees over its time of operation. Such environmental temperature changes have the propensity to change the operating parameters of an electrical inductance coil, such as the probe used in the present invention. The disclosed time multiplex filter circuit compensates for the parameter changes of the inductance coil probe by utilizing a unique time multiplexing system to factor out any error caused by temperature change.

It is the principal object of the present invention to provide a ferrous particle capture device for use in a circulating liquid system wherein the mass of the total accumulated particles so captured are measured. It is a further object of the present invention to provide signals suitable for analog or digital display, the amplitude of which is a function of the mass accumulated on the particle capturing device for the estimation of the amount of material accumulated. It is also the object of the present invention to provide a temperature compensating means to increase the accuracy of the signal generated which represents the mass of the total accumulated particles captured over a wide increase or decrease in ambient temperature of the probe.

DETAILED DESCRIPTION OF THE INVENTION

The present invention utilizes debris collection means such as that disclosed in patent Ser. No. 4,731,578 issued on 3/15/88 entitled "An Electrical Sensing System for Measuring Ferrous Particles Within a Fluid". The disclosure set forth in that application, filed by one of the inventors named above, is incorporated herein by reference.

The present invention is a method of collecting and measuring the quantity of ferrous particles suspended in a fluid such as lubricating oil in a transmission. It is desirable to monitor the amount of ferrous particles or debris which may be suspended in a lubricating fluid such as transmission oil in a gear box or internal combustion engine. To collect such ferrous material at a location to perform such monitoring, it is desirable to place a permanent magnet within the fluid to attract such particles. Once such ferrous particles begin to collect on a magnetic surface, they can be further measured so that it may be determined what total amount of ferrous particles may be suspended in such fluid. The presence of such ferrous particles frequently indicates impending mechanical failure.

Upon collection of the ferrous particles upon a magnet, it is possible to measure the quantity of such particles by introducing an electrical inductor in the vicinity of such ferrous particles. It is well known that changing the core material in the proximity of an electrical inductor will cause a change in the inductance value of that inductor. Therefore, measuring the inductance change of an electrical coil in the vicinity of a collection of ferrous particles upon a magnet can provide an input means to ultimately measure the amount of such particles being collected.

Figure 5:
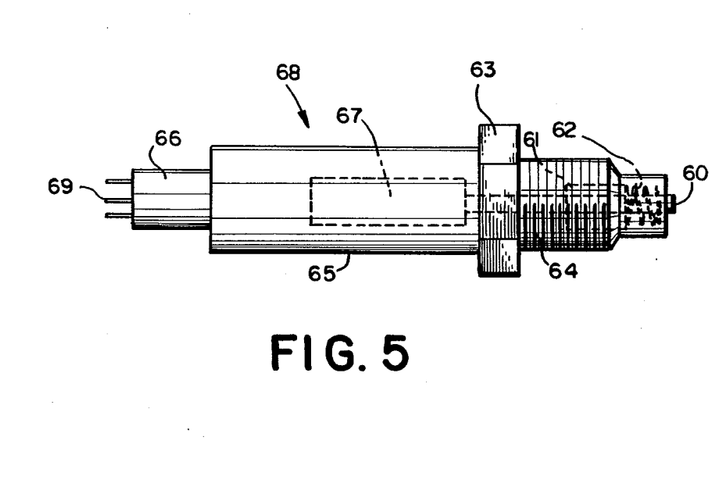
FIG. 5 is a view of the type of sensor probe to be used for insertion within a reservoir of fluid containing ferrous particles to be measured.

Turning to FIG. 5 of the drawings, an electrical sensor plug 68 for collecting ferrous particles within the fluid is shown. A sensor 68 is essentially designed as a plug, such as a drain plug one may find on any fluid carrying vessel, particularly oil sumps and transmission gear oil boxes as found in many different transmission and internal combustion engine systems. Sensor 68 is comprised of the sensor body 65, with an integral wrench nut 63 for fastening the sensor into a frame. Such fastening is facilitated by the surface thread 64 which are threaded to allow the sensor to be bolted into the wall of the container of the fluid to be observed. Magnet 67 is contained within the body of sensor 68. Magnet 67 is a permanent magnet, but does not actually extend through the threaded portion of sensor 68 to the collection surface 60. Magnetic flux is transmitted to collection surface 60 through pole piece 61. Pole piece 61 serves to extend magnetic flux from magnet 67 to collection surface 60 without actually requiring the magnet 67 to be located at the end of sensor 68 which actually protrudes into the fluid to be measured.

Coil 62 is formed within the housing 68 at a location set forth in FIG. 5. This inductor 62 is coaxial with pole piece 61 and is formed so that collection of ferrous material on collection surface 60 serves to alter the inductance of coil 62 by the change in the permeability of the core of 62. It will be appreciated by those skilled in the art that a collection of ferrous material in a location close to an electrical inductor will increase the value of that inductor. In the sensor configuration shown in FIG. 5, the lines of flux produced by magnet 67, transmitted through pole piece 61 to collection surface 60, create an attractive magnetic zone in the vicinity of the collection surface 60. When a ferrous particle enters the magnetic zone and is captured on the collection surface 60 it will be appreciated that such would change the inductance value of coil 61. Coil 61 is connected through two leads, not shown, through the housing 65 to electrical connector 66. Electrical connector 66 is a conventional electrical plug with prong 69 protruding therefrom. Two leads of prong 69 represent the leads from both sides of the coil. The third lead of prong 69 is a grounding prong which is attached ultimately to housing 65. This grounding prong allows a shielded cable to connect coil 62 with any external electronic circuitry as will be described below.

The present invention includes a method of determining, and correcting for, error and drift in the resonant RLC circuit which may be caused by temperature or other physical or environmental changes. The circuit, in it operation which will be described below, may be utilized in conjunction with sensor 68 to provide an accurate reading of the accumulation of ferrous debris on surface 60.

It is well known that a parallel RLC network has a resonant frequency which is approximated by the relation $$f_0 = \frac{1}{2\pi \sqrt{LC}}$$

In such a parallel RLC network, the impedance of such a network, as measured across the network, is at a maximum at the resonant frequency of the network. When such a parallel resonant circuit is driven by a constant current, the voltage developed across the network reaches a maximum when the network is driven at the network's resonant frequency as described by the equation above.

Figure 2:
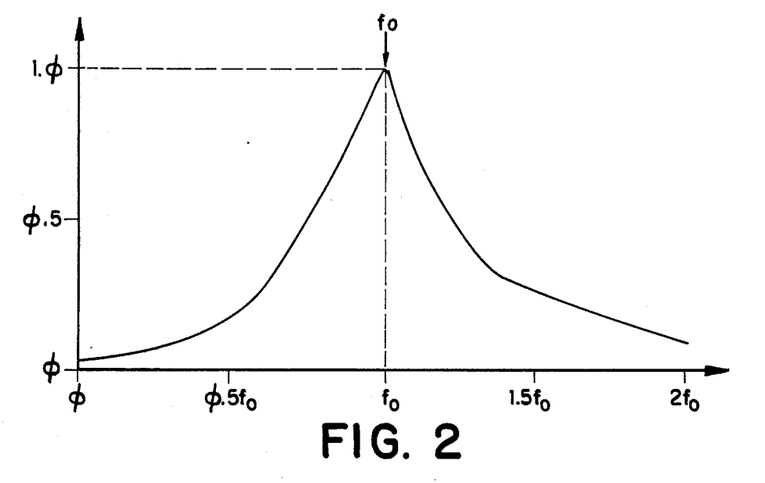
FIG. 2 is a graph representation of the frequency response of a parallel tuned circuit, plotted with voltage amplitude across the tuned circuit on the Y axis and the drive frequency being applied to the circuit represented on the X axis.

FIG. 2 depicts a well known frequency response curve of an RLC network. The resonant frequency of the network is depicted as $f_0$, shown as 86 on FIG. 2. As the driving frequency of the circuit is increased or decreased above or below point 86, it will be appreciated that the voltage measured across such a network decreases.

If the parallel resonant were to be driven at a frequency other than its resonant frequency $f_0$ (86), the voltage measured across the network will be lower than the maximum value found at the resonant frequency. This would be the case regardless of whether the drive frequency was above or below the resonant frequency $f_0$ (86).

Figure 3:
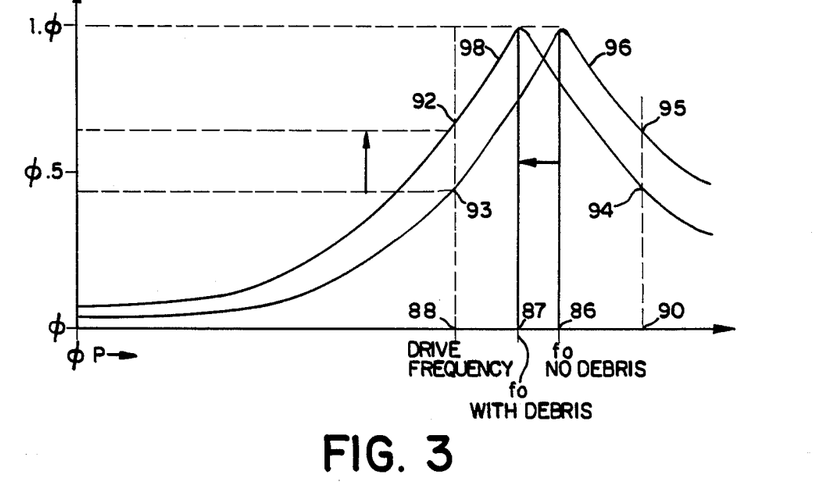
FIG. 3 is a graph representation of the frequency response of a parallel tuned circuit, for two different values of components in the tuned circuit. The frequency response curve shown in FIG. 3 represent the same tuned circuit with the resonant frequency shifted downward due to the change of the inductance.
Figure 4A:
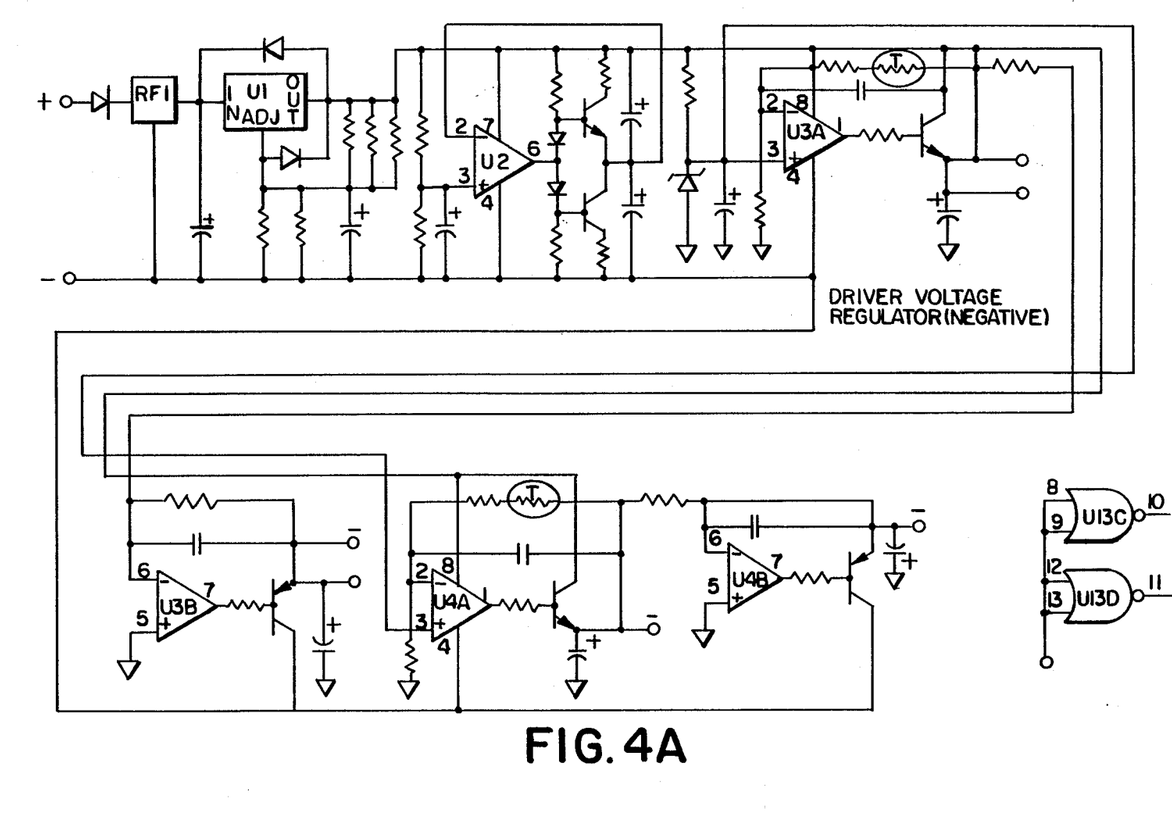
FIG. 4A-4F are an electronic schematic diagram illustrating electronic component placement and selection for the preferred embodiment of the present invention.
Figure 4B:
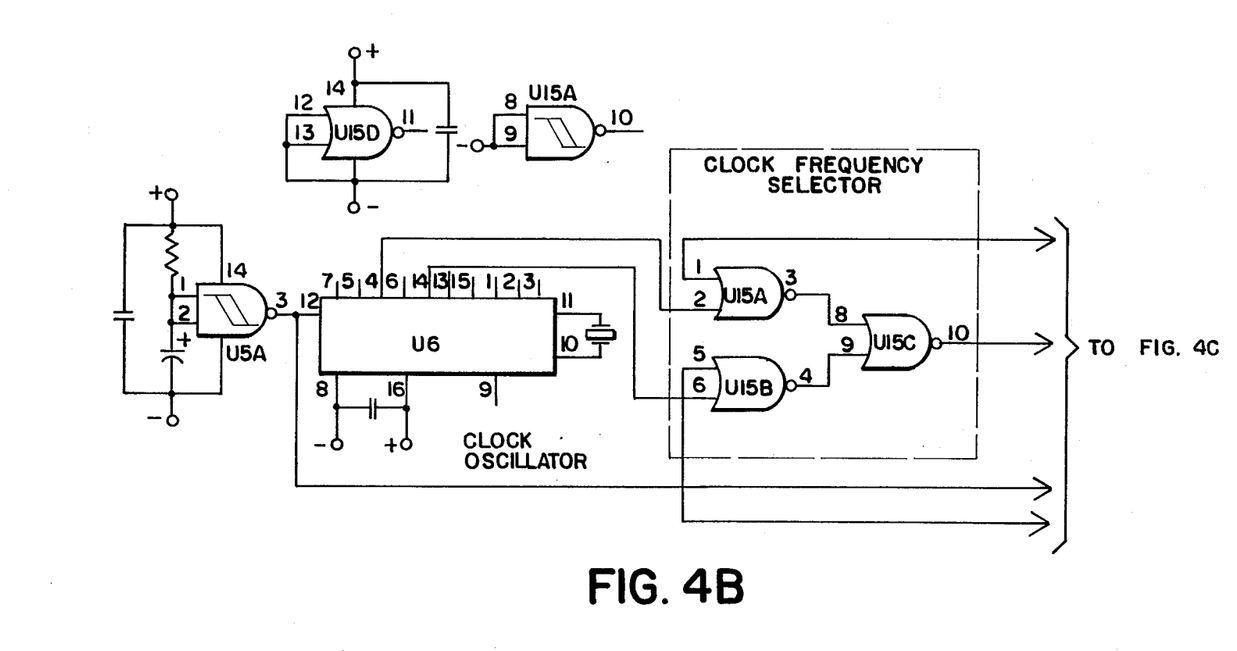
Figure 4C:
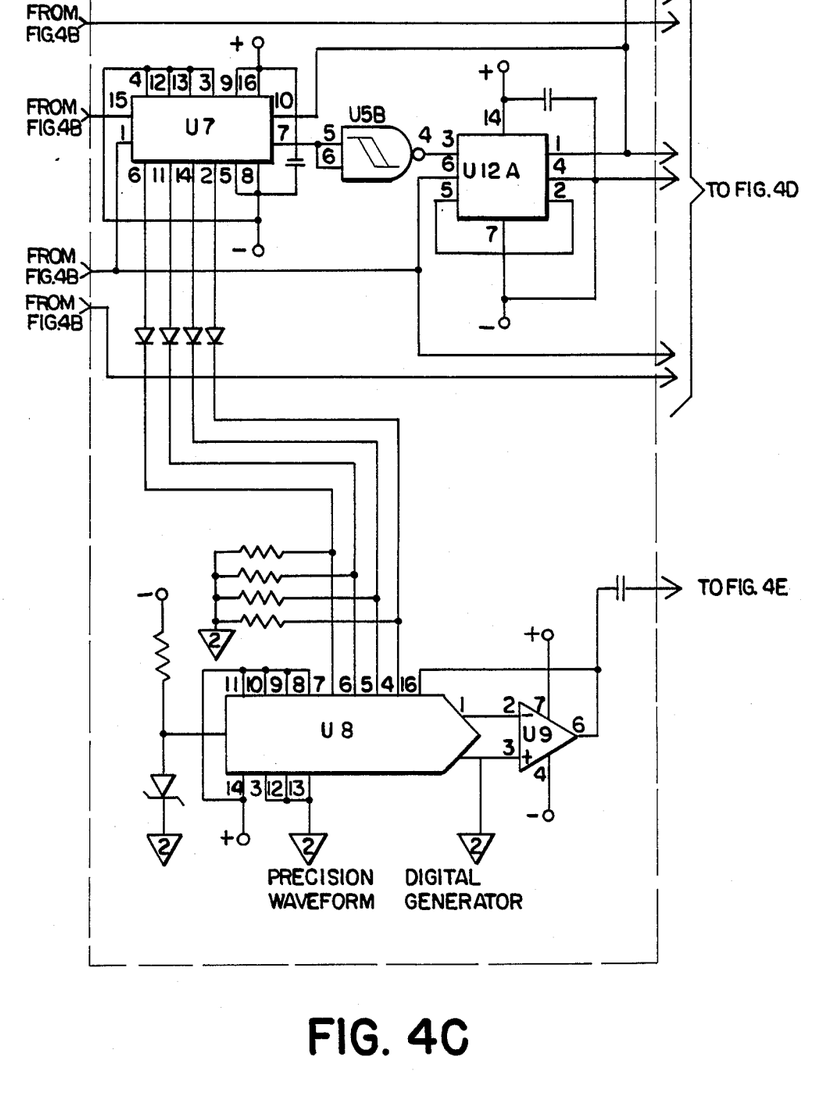
Figure 4D:
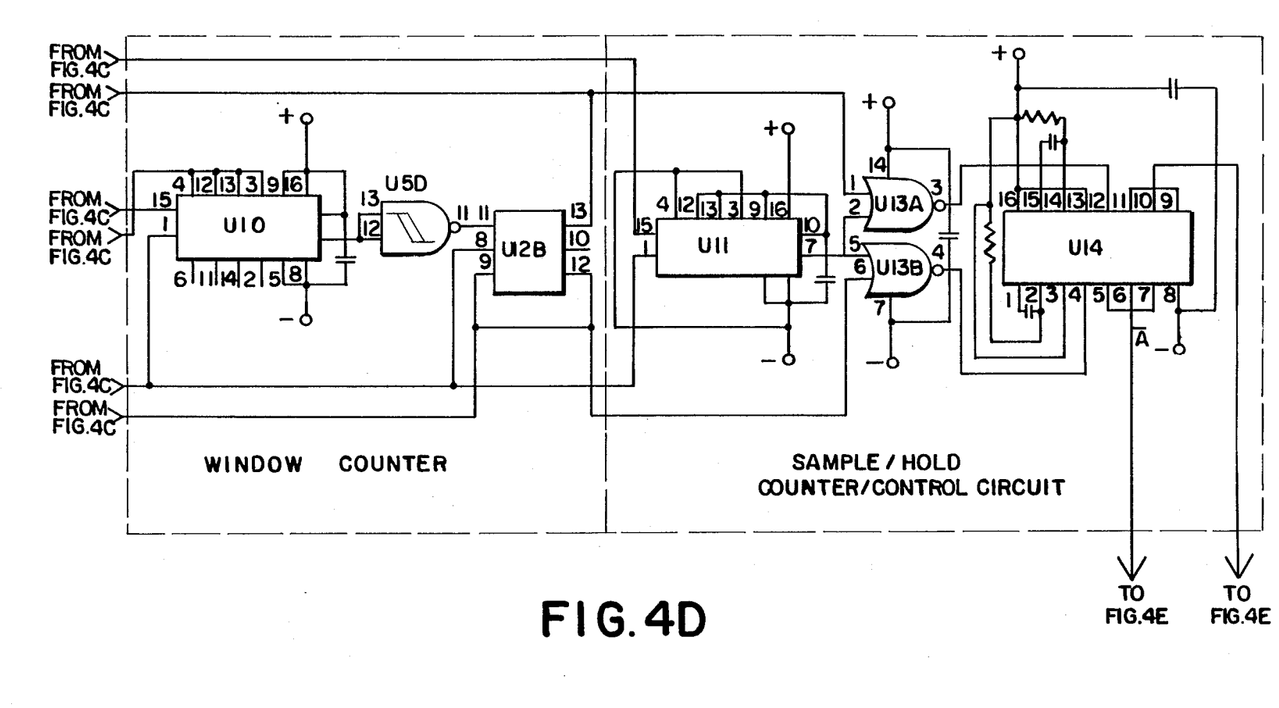
Figure 4E:
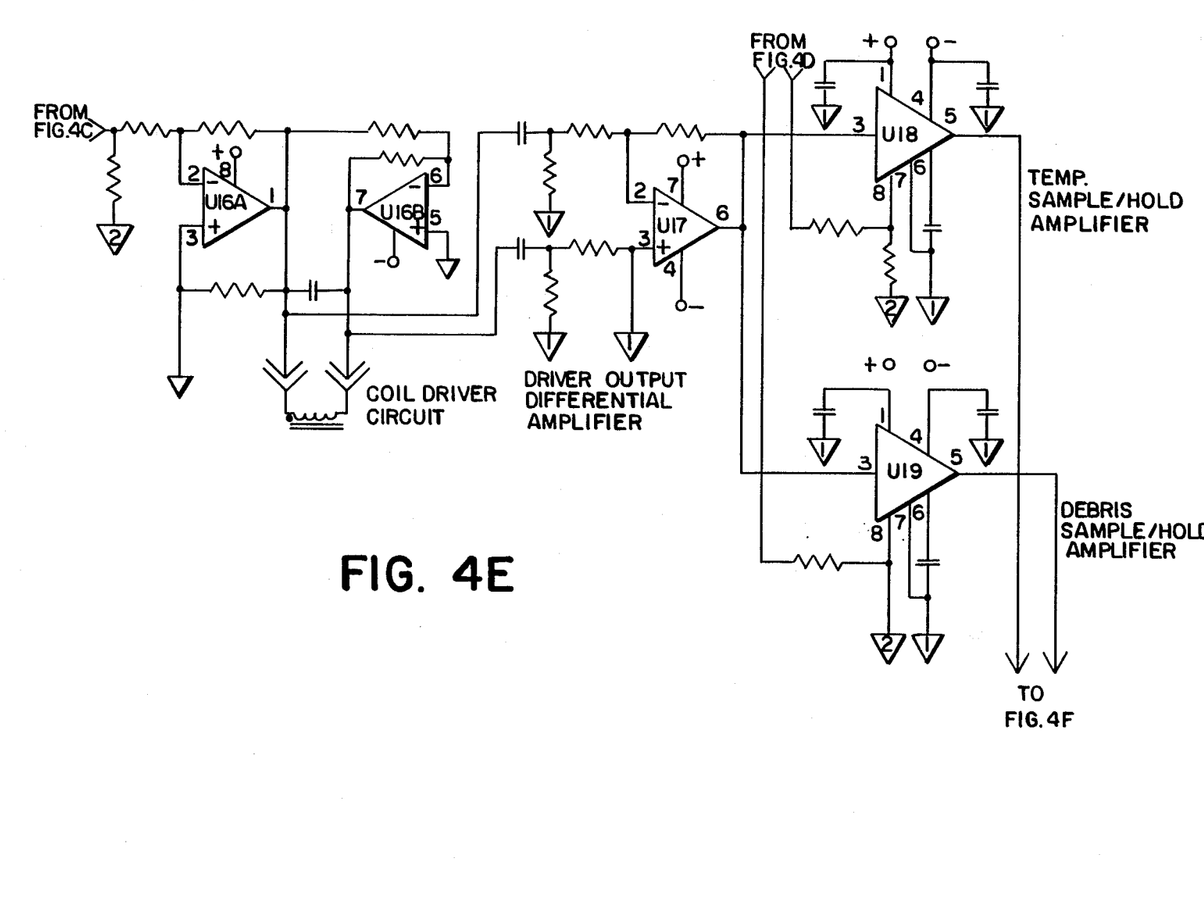
Figure 4F:
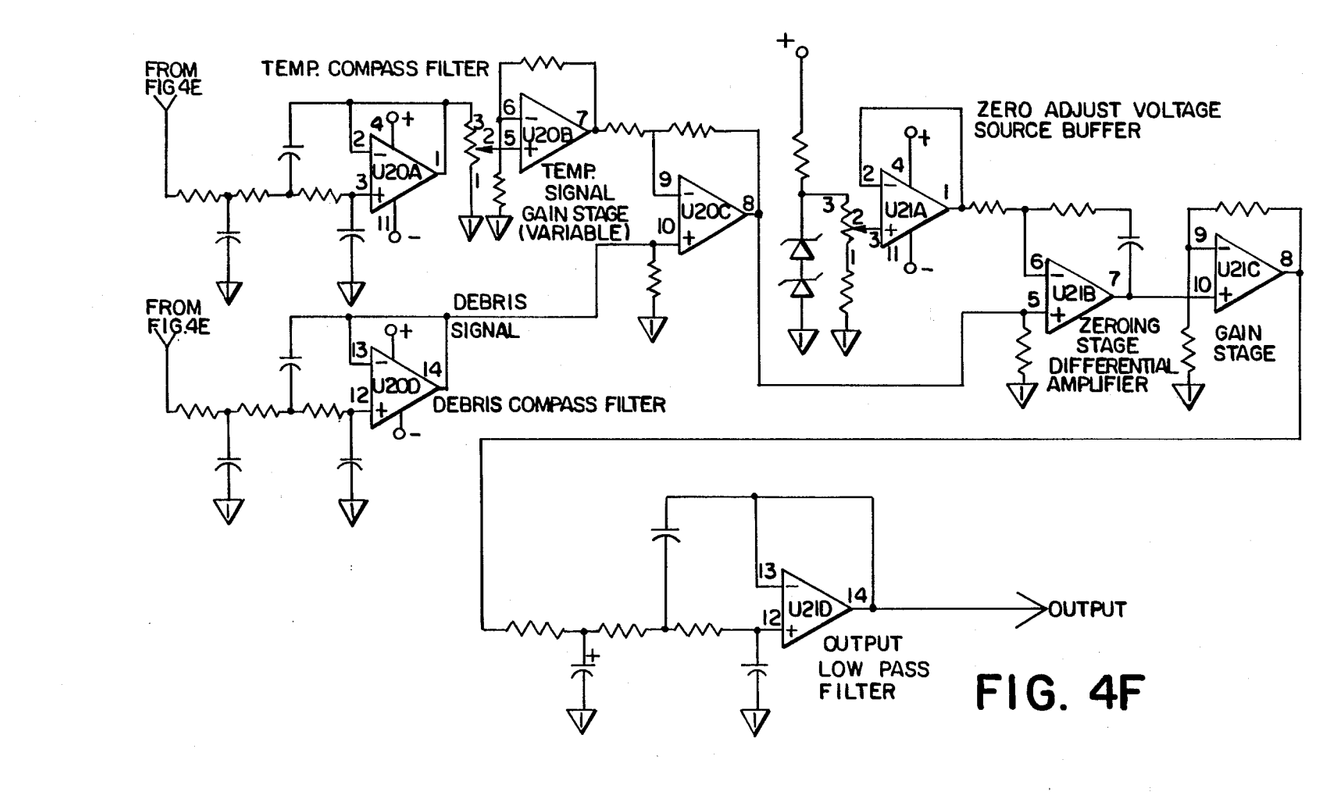

Turning to FIG. 3, the change in the voltage amplitude vs. frequency is depicted by two curves, 96 and 98, superimposed on the same graph. The two curves shown illustrate the same frequency response of the RLC network. However, curve 98 has been shifted slightly in frequency by a change in the value of the inductance which comprises an RLC network. If the inductance of the RLC network were to change, due to the change in the value of the core of the coil 62 in FIG. 5 caused by debris accumulation, the resonant frequency of RLC network would shift from $f_0$ shown at 86 to $f_0$ shown at 87. If the RLC network was being driven at a frequency $f_1$, shown at 88 on FIG. 3, it will be appreciated that a shift in the resonant frequency of the network being measured from 86 to 87 will cause an increase in voltage across such a network. The voltage measured across the network with resonant frequency 86, when driven at a drive frequency below resonance depicted by 88, would be measured to be a value shown as 93 on FIG. 3. If the resonant frequency of the RLC network were to be shifted to a frequency value shown as 87 on FIG. 3, the voltage measured across the RLC network would increase to value 92 shown on FIG. 3. Similarly, if the RLC network being measured were driven at a frequency 90 higher than its resonant frequency 86, the voltage across the network would be less than maximum as shown at 95 on FIG. 3. If the RLC network resonant frequency were to be shifted downward to frequency 87, the voltage across the RLC network would decrease to value 94. In summary, given a drive frequency below resonance 88, and a drive frequency above resonance shown at 90, the voltage across the RLC network, when such resonant frequency is shifted downward would increase at frequency 88 and decrease at frequency 90.

Figure 1:
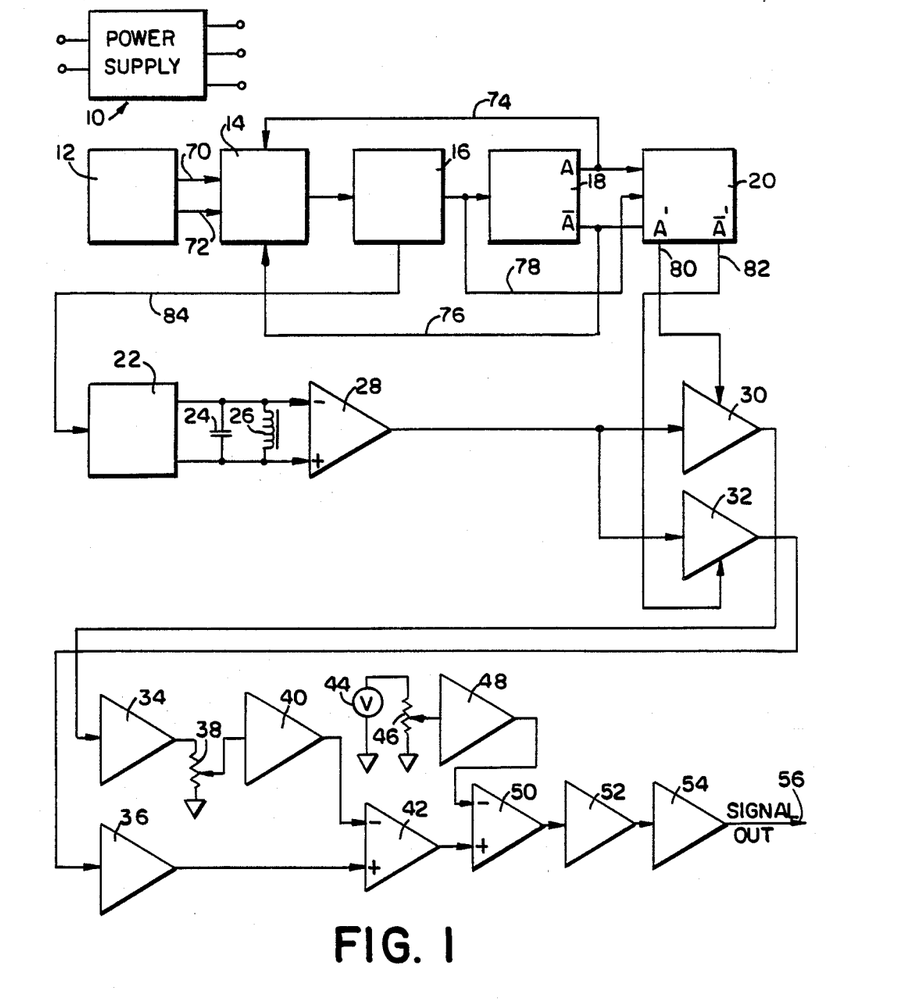
FIG. 1 is an electronic block diagram illustrating the major components of the invention, and is a simplified illustration of the schematic diagram found in FIG. 4.

If the change in frequency from 86 to 87 shown in FIG. 3 is measuring the amount of debris accumulation on collection surface 60, it is desirable to have such a change occur only in response to the resulting inductance change exhibited by coil 62, and not due to other external parameters, such a temperature. It is well known that a temperature variation in an electronic component can and will cause a change in the components designed parameters. Frequently these undesirable environmental changes are sufficient to cause a substantial error in the parameter being measured through the change of such component, such as the inductance in the RLC network. In the preferred embodiment of the present invention, the value of inductor L in the resonant circuit is altered by an increase in the permeability of the core of coil 62 in sensor 68. Such an increase in permeability, causing a corresponding increase in the inductance value of L in coil 62, is related directly to the amount of ferrous debris accumulation. Assuming the change in inductance of coil 62, represented as inductance 26 in FIG. 1, is to be measured by measuring the voltage change across a resonant network, while driven at a given frequency, any voltage change across that network caused by some other parameter would be undesirable. Change in the reactance of the RLC circuit 25 due to temperature, is undesirable as interfering with the desired input change of coil 62. The present invention offers a system to correct for this assumed undesirable first order change due to temperature. The electronic circuit described teaches a method which factors out any change in the voltage vs. frequency response of the RLC circuit, driven at a given frequency, by factors other than the actual desired change due to the control input.

In the preferred embodiment of the present invention, it will be assumed that the error to be corrected is a change in the resistance of coil 62 due to temperature, and that the temperature compensation desired is to counter the effect of a temperature change due to the change in the fluid temperature. The compensation method utilized in the present invention is the time multiplexing of two frequencies, described earlier and illustrated on FIG. 3 as frequency 88 and frequency 90, being above and below the resonant frequency of the RLC network, either 86 or 87 as shown on FIG. 3. By driving the RLC network alternatively in time, at frequency 88 or frequency 90, at predetermined lengths of time, the voltage across the RLC network can be measured during each event. The voltage change across the network will be in opposite directions if such change is due to a change in the resonant frequency from 86 to 87 as shown in FIG. 3. Such a change will cause the voltage across the network to increase from 93 to 92 at frequency 88. As described earlier, the same change in resonant frequency from 86 to 87 would cause a decrease of voltage across the network from 95 to 94 at frequency 90 in FIG. 3. However, it will be appreciated that a change in the characteristic reactance of an RLC network, due to temperature, mainly alters the resistance which shifts the relative voltage amplitude across the network causing either an increase or decrease, but in a direction which is identical, whether driven at frequency 88 or 90. An increase in resistance, for example, of the RLC network will cause the voltage amplitude value of curve 96 and curve 98 to decrease at all values across increase or decrease in voltage across the network which is in the same direction, either at frequency 88 or at frequency 90, would allow such a change to be factored out from any voltage change which is due to altering the inductance value of the RLC circuit. The present invention discloses a method for measuring such changes.

FIG. 1 depicts a complete system for filtering the undesirable first order changes described to the extent that a signal output presented by the system depicted in FIG. 1 will represent only the desired change in inductance of the parallel RLC network under measurement.

In FIG. 1, a clock oscillator 12 is designed to operate at two frequencies, corresponding to lower frequency 88 and higher frequency 90 shown on FIG. 3. The high frequency 70 of the clock oscillator is introduced into the clock frequency selector 14. In a similar fashion, the low frequency signal from clock oscillator 12 is introduced into clock frequency selector 14 through line 72. The clock frequency selector 14 is controlled by selection input paths 74 and 76 which will be described below. It will be appreciated that clock frequency selector 14 is a switch which selects either the high frequency 70 or low frequency 72. The output of 14 is introduced into a precision digital waveform generator 16 which has two outputs, one of which is introduced into a window counter 18 and the other which is introduced into a coil driver circuit 22 through path 84. Window counter 18 is a timing device which controls clock frequency selector 14 through paths 74 and 76. The waveform generator 16 driving window counter 18, in effect, controls the switching of window counter 18 to select the high frequency output of clock 12 or the low frequency output of clock 12. An output of the precision digital waveform generator 16 is also introduced through path 84 into the coil driver circuit 22 which, in the preferred embodiment, is a Howland constant current source. The output of generator 16 through path 84 is not actually the same frequency as the clock oscillator 12 outputs at 70 or 72. Output 84, while necessarily proportional to output 70 or 72, is of a lower frequency and is switched in accordance with whether selector 14 has selected output 70 or 72. For the operation of the present invention, it is important that driver circuit 22 is a constant current source to avoid other undesirable voltage changes across network 25 and the design and construction of such is well known to those skilled in the art.

The RLC network described earlier is shown as 25 in FIG. 1. Essentially, capacitor 24 is in parallel with inductor 26. In the present invention, inductor 26 in FIG. 1 is equivalent to coil 62 in FIG. 5. Coil 62 is connected by shielded electrical conductors to the circuit shown in FIG. 1 so that it is actually remotely located in sensor 68. By utilizing shielded cable to remote inductor 26, as coil 62 in FIG. 5, the electrical effects in the value of the inductance due to the connecting cable are essentially eliminated. In such circuits, there is always inherent resistance across both capacitor 24 and inductance 26 although it is not shown in the system diagram on FIG. 1. Such a resistance may be the internal resistance of the components or an implied resistance, by design, across such circuit 25. The output of the RLC circuit 25 is introduced into a driver output differential amplifier 28. The output of amplifier 28 is a signal representing the change in voltage across the input of amplifier 28, which itself represents the change in voltage across the RLC Circuit 25. The output of 28 is introduced both into sample and hold amplifier 30 and sample and hold amplifier 32. As can be seen in FIG. 1, the sample and hold amplifier 30 is controlled by counter control 20 through path 80. In a similar fashion, sample and hold amplifier 32 is controlled through path 82 by the control counter 20. The sample and hold amplifier that is operating at any one particular time is a function of whether the high frequency of clock 12 or the low frequency of clock 12 is being selected. The window counter 18 controls sample and hold counter control 20. As the frequency input to the system, either the high frequency 70 or the low frequency 72, is alternatively selected in time, it will be appreciated the either the sample and hold amplifier 30 will be operating or sample and hold amplifier 32 will be operating. In this method, the output of 28 can be measured for both the low frequency signal and the high frequency signal. The output of amplifier 32 represents the output of the desired measured change of the inductance 25, representing the voltage drop across the RLC circuit 25 for a low drive frequency 72, also represented in FIG. 3 at 88. The output of 32 is introduced into a low pass filter 36 which is utilized to remove noise and other extraneous signals which may be generated because of the switching process inherent in the system described. The output of the low pass filter 36 is introduced into differential amplifier 42 which compares such input with the error signal being introduced into the inverting input of amplifier 42 as will be described below.

Returning to the remaining sample and hold amplifier 30, this amplifier samples and holds the output from differential amplifier 28 when commanded by the counter control 20 through line 80. This sample and hold amplifier 30 is commanded to operate during the period of time when clock 12 is generating a high frequency.

The output of amplifier 30 is introduced into a low pass filter 34 which, similar to the low pass filter 36, is utilized to filter noise and other extraneous inputs generated through switching transients and the like. The output of the low pass filter 34 is introduced into amplifier 40, whose gain is controlled through input level adjustment found through potentiometer 38. It will be appreciated that amplifier 40 can be utilized to amplify the error signal introduced out of low pass filter 34 to a suitable level for introduction into the inverting input of differential amplifier 42.

The temperature compensating function described in the preferred embodiment occurs because the desired change in inductance in L causes an increase in the amplitude of the output of amplifier 28, at frequency 88 less than the frequency 87, being lower in value than the starting resonant frequency $f_0$ at 86, and a decrease in the output of amplifier 28 when the RLC network is being driven at a frequency above resonance, shown by example at 90. However, the direction of change of the amplitude of the output of amplifier 28, with respect to an increase of temperature, will be the same regardless of whether frequency 88 or 90 is being selected. The control signals generated by counter controller 20 are designed so that both have either a positive or negative temperature coefficient, depending on the direction of error correction of the output of sample and hold 32 which is desired. In the preferred embodiment, a negative temperature coefficient was chosen although a positive temperature coefficient can be utilized by a minor change in the circuit design which can be accomplished by a simple change in a component value.

Returning to compensation differential amplifier 42, it will be appreciated that the output of this amplifier is the inductance signal, represented at the output of filter 36, minus the amplified error signal which is represented by the output of amplifier 40. In short, the output of 40 is subtracted from the output of 36. The effect of this operation is that the desired signal representing the change in inductance (of inductance 26, also coil 62 in sensor 68) will be added together, since the signals are opposite and would arithmetically add. However, the voltage component inherent in the output of filters 34 or 36 which represents the error signal, by the design of the circuits shown, will have the same value sign and therefore, would cancel out.

Returning to FIG. 3 momentarily to describe this effect, it would be appreciated that a resistance change affecting the voltage drop across network 25, due to temperature, will reduce the output seen from amplifier 28 from the point represented by 92 slightly downward in the direction of point 93. At frequency 90, however, the output of 28 would decrease slightly from the voltage amplitude represented by 94, lower towards the F axis of FIG. 3. Through the circuit as described, this temperature change is cancelled out through the operation of amplifier 42, leaving only the output of 42 representing the value of the inductance change in the resonant circuit. The resultant desired signal, at the output of amplifier 42, is adjusted to zero through the use of a zeroing stage differential amplifier 50. It will be seen that a constant voltage source 44, the fixed magnitude of which can be varied by potentiometer 46, is introduced into a voltage source buffer 48. The output of buffer 48 is applied to the inverting input of differential amplifier 50 such that the resting output of the disclosed circuit can be set to zero as may be desired. In this fashion, only actual changes in inductance 26 which result from the desired control input will be presented to gain stage 52, the output of which is introduced to a low pass filter 54. Low pass filter 54 removes noise and short term changes then produces the output signal 56 which is the desired signal, absent any undesired change due to temperature variation as described.

Finally, power supply 10 shown in FIG. 1 is of a conventional design, and is utilized to operate the various stages shown in FIG. 1 as may be required. In the preferred embodiment, a 28 volt input to power supply 10 produces various outputs, of 7.5 volts, either positive or negative as may be desirable. The design and operation of a power supply for operating an electronic circuit is well known to those skilled in the art and is not unique or specific to the present invention. Turning now to FIG. 4A-4F, an actual schematic diagram of the circuit as constructed in the preferred embodiment is disclosed. The circuit shown operates on a 28 volt DC input nominal, has various discrete and integrated electronic components shown in its construction. The schematic diagram disclosed in FIG. 4A-4F is a detailed description of the block diagram circuit set forth in FIG. 1.

The output signal derived at point 56 in FIG. 1 can be processed using conventional electronics to display the resulting signal. It will be appreciated that the signal output at 56 will be proportional to the debris accumulation present on collection surface 60. Signal 56 can be used to trigger an alarm signal at some predetermined threshold level, or may be continuously monitored by conventional analog or digital display means so that the actual value of signal 56, scaled to represent a measured quantity of the actual amount of ferrous debris being collected, may be observed by the vehicle operator.

Although the present invention has been described with reference to the particular embodiments herein set forth, it is to be understood that the present disclosure has been made only by way of example and that numerous changes in the details of construction may be resorted to without departing from the spirit and scope of the invention. Thus, the scope of the invention should not be limited to the foregoing specification, but rather only by the scope of the claims appended hereto.

What is claimed is:

1. A means for sensing ferrous contamination in a fluid comprising:
    (a) a generally cylindrical magnet;
    (b) an electrical coil located co-axially on one end of said magnet, said coil having a hole lengthwise through its center;
    (c) a pole piece of said magnet occupying the hole in said first coil and concentric with said magnet disposed at one end of the magnet, said pole piece of the magnet being available to accumulate ferrous contamination present in a fluid whereby any ferrous accumulation changes the induction of the coil;
    (d) An electronic circuit means for measuring inductance changes of said electrical coil including;
        a clock oscillator means providing two discrete frequencies, one high frequency and one low frequency;
        a frequency selection means to select, upon command, one of the two frequencies of the said clock oscillator means;
        a waveform generator;
        a waveform period counter which switches between one of two states corresponding to said high frequency and said low frequency of said clock oscillator;
        a sample and hold counter control means operatively connected to said waveform period counter;
        a first sample and hold amplifier;
        a second sample and hold amplifier;
        a constant current coil driver circuit driving a tuned circuit having a resonant frequency between said high frequency and said low frequency, said tuned circuit including said electrical coil;
        a first differential amplifier; and
        a second differential amplifier;
    wherein said clock oscillator is operatively connected to the frequency selection means, and said frequency selection means alternatively selects said high and low frequency from said oscillator means to introduce such frequency into the waveform generator, said waveform generator producing a frequency output proportional to the said selected high or low frequency and introducing said proportional output to the said coil driver constant current circuit, and the said waveform period counter;
    wherein further said constant current driver provides a constant current to said tuned circuit, the output of said tuned circuit being placed across the input of said first differential amplifier such that the output of said amplifier represents the voltage across said tuned circuit;
    the output of said amplifier being introduced to the input of said first and second sample and hold amplifiers, said first sample and hold amplifier driving an inverting input of said second differential amplifier and said second sample and hold amplifier driving a non-inverting input of said second differential amplifier said second differential amplifier providing an output proportional to inductance changes of said electrical coil;
    wherein further said first and second sample and hold amplifiers are commanded through said sample and hold counter control means to sample and hold by said waveform period counter in a manner corresponding to said high frequency and said low frequency of said clock oscillator means.

2. The means for sensing ferrous contamination in a fluid as in claim 1 further comprising an adjustable voltage source and a third differential amplifier with the non-inverting input of said third amplifier operatively connected to the output of the second differential amplifier and said adjustable voltage source is connected to the inverting input of said third differential amplifier.

3. The means for sensing ferrous contamination in a fluid as in claim 2 further wherein the output of said third differential amplifier is operatively connected to a further stage of amplification which provides low-pass filtering.

* * * * *